US009149205B2

United States Patent
Hancu et al.

(10) Patent No.: US 9,149,205 B2
(45) Date of Patent: Oct. 6, 2015

(54) BREAST COIL FOR USE IN MAGNETIC RESONANCE IMAGING

(71) Applicant: General Electric Company, Schenectady, NY (US)

(72) Inventors: Ileana Hancu, Clifton Park, NY (US); Kenneth William Rohling, Schenectady, NY (US); Luca Marinelli, Schenectady, NY (US); Eric William Fiveland, Niskayuna, NY (US); Seung-Kyun Lee, Cohoes, NY (US); Keith J. Park, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 244 days.

(21) Appl. No.: 13/852,723

(22) Filed: Mar. 28, 2013

(65) Prior Publication Data

US 2014/0296701 A1    Oct. 2, 2014

(51) Int. Cl.
   *A61B 5/05*       (2006.01)
   *A61B 5/055*      (2006.01)
   *A61B 5/00*       (2006.01)

(52) U.S. Cl.
   CPC .............. *A61B 5/0555* (2013.01); *A61B 5/708* (2013.01)

(58) Field of Classification Search
None
See application file for complete search history.

(56) References Cited

U.S. PATENT DOCUMENTS

| 5,548,218 | A | * | 8/1996 | Lu .................................. 324/318 |
|---|---|---|---|---|
| 6,889,073 | B2 | | 5/2005 | Lampman et al. |
| 7,498,813 | B2 | | 3/2009 | Giaquinto et al. |
| 7,715,895 | B1 | | 5/2010 | Graessle et al. |
| 8,078,260 | B2 | | 12/2011 | Brasile |
| 8,217,653 | B2 | | 7/2012 | Vaughan |
| 8,366,617 | B2 | | 2/2013 | Johnson et al. |
| 2007/0016003 | A1 | * | 1/2007 | Piron et al. ..................... 600/415 |
| 2008/0214930 | A1 | | 9/2008 | Brasile |
| 2009/0082662 | A1 | | 3/2009 | Israel |
| 2009/0216110 | A1 | * | 8/2009 | Piron et al. ..................... 600/415 |
| 2010/0099978 | A1 | | 4/2010 | Geppert et al. |
| 2010/0141260 | A1 | * | 6/2010 | Schilling ........................ 324/322 |
| 2010/0298693 | A1 | | 11/2010 | Dietz et al. |
| 2010/0315085 | A1 | | 12/2010 | Brown et al. |
| 2011/0241683 | A1 | | 10/2011 | Nnewihe et al. |
| 2014/0213886 | A1 | * | 7/2014 | Menon et al. .................. 600/411 |

OTHER PUBLICATIONS

Jeufack et al., "Parallel Imaging Performance of 16 Channels Dedicated Breast Coils at 3T", Europen Society of Radiology, 2010, pp. 1-12.*

International Search Report and Written Opinion issued in connection with corresponding PCT Application No. PCT/US2014/031720 dated Aug. 14, 2014.

(Continued)

*Primary Examiner* — Christopher Cook
(74) *Attorney, Agent, or Firm* — Melissa K. Dobson

(57) ABSTRACT

The present disclosure relates to a receive coil assembly for use in magnetic resonance imaging of breast tissue. In certain embodiments the assembly comprises separable parts: a configurable mechanical support and a flexible receive coil array. The adjustability and separability of the receive coil array relative to the mechanical support allows the receive coil array to substantially conform to the breasts of the patient during imaging.

13 Claims, 6 Drawing Sheets

(56) References Cited

OTHER PUBLICATIONS

Artemov, Dmitri, et al., "Switchable Multicoil Array for MR Micro-Imaging of Breast Lesions", Magnetic Resonance in Medicine, vol. 41, pp. 569-574, 1999.

Marshall, H., et al., "Evaluation of multi coil breast arrays for parallel imaging", Journal of Magnetic Resonance Imaging, vol. 41, pp. 569-574, Feb. 2010.

* cited by examiner

BREAST COIL FOR USE IN MAGNETIC RESONANCE IMAGING

STATEMENT REGARDING FEDERALLY SPONSORED RESEARCH & DEVELOPMENT

This invention was made with Government support under contract number 1R01CA154433 awarded by the National Institute of Health (NIH). The Government has certain rights in the invention.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Magnetic Resonance Imaging (MRI) systems enable imaging based on a primary magnetic field, a radio frequency (RF) pulse, and time-varying magnetic gradient fields that interact with specific nuclear components in an object, such as hydrogen nuclei in water molecules. The magnetic moments of such nuclear components may generally align with the primary magnetic field, but subsequently precess about the bulk magnetic field direction at a characteristic frequency known as the Larmor frequency. An RF pulse at or near the Larmor frequency of such nuclear components may cause their magnetic moments to be rotated. When the RF pulse has ended, the magnetic moments relax and generally align with the primary magnetic field, emitting a detectable signal.

MRI may be particularly useful for obtaining certain physiologic and anatomic information. For example, unlike imaging techniques that are based on the differential attenuation of radiation through the body, MRI provides images that convey information about the imaged area that is not based on the relative radiation attenuating properties of the tissue. Instead, MRI provides images that are based on the respective magnetic properties of the anatomy undergoing imaging, and thus may provide images where soft tissue structures can be meaningfully differentiated, such as based on fat content, water content, and so forth. In addition, certain MRI techniques allow visualization of diffusion phenomena within the body and allow other functional characteristics of a tissue to be observed.

As a result, MRI may be a useful imaging technology for certain medical purposes. For example, MRI may be a useful tool for cancer screening or monitoring due to its ability to differentiate soft tissue structures. One area where use of MRI techniques may be of particular interest is in screening for or monitoring breast cancer, due to the discomfort and radiation dose associated with conventional mammography. However, conventional breast array receive coils for use in MRI fail to properly conform to many patients, which can result in a decrease in the effective signal-to-noise ratio. Thus, poor signal-to-noise ratio is an impediment to increasing the use of MRI in the detection of breast cancer

BRIEF DESCRIPTION

In one embodiment, a breast imaging assembly for use in a magnetic resonance imaging system is provided. The assembly comprises a mechanical assembly and an electrical assembly that is separable from the mechanical assembly. The mechanical assembly comprises: a patient facing surface configured to support a patient in a breast imaging position and an opening within the patient facing surface through which the breasts of the patient pass when the patient is supported by the mechanical assembly. The electrical assembly comprises: a flexible substrate configured to removably couple to the mechanical assembly and a plurality of receive coils embedded within the flexible substrate.

In a further embodiment, a mechanical support for breast imaging is provided. The mechanical support comprises a housing component that in turn comprises a patient facing surface; an opening defined in the patient facing surface; and a lateral opening on either side of the opening. The mechanical support further comprises a sternum support configured to fit within the opening such that, when fitted within the opening, the sternum support divides the opening into two respective portions. In addition, the mechanical support comprises a flexible support configured to move with respect to the housing component so as to allow the lateral opening to be opened or closed on one or both sides of the housing component.

In an additional embodiment, a receive coil array for use in breast imaging is provided. The receive coil array comprises a flexible substrate capable of conforming to the surfaces of a patient's breast when in use. The receive coil array further comprises a plurality of receive coils formed within the flexible substrate. The plurality of receive coils is greater than eight in number.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

High temporal resolution dynamic contrast enhanced (DCE)-MRI imaging (which enables good kinetic data modeling) and high resolution diffusion weighted imaging (DWI) are two techniques used in breast MRI for cancer detection. Such techniques may be limited by the signal-to-noise ratio obtained in a given imaging session. For example, DWI is usually performed using EPI acquisitions. However, the long echo times of such scans reduce the image (SNR), therefore limiting the spatial resolution of the images. Further, the typical 8-30 μl DWI voxel volume, when combined with a poor SNR, makes image interpretation difficult and hampers the detection of small lesions.

While increasing the channel count of a breast receive array may be desirable to improve image SNR in such contexts, the design of a suitable array geometry for the breast anatomy may be difficult. In particular, since breast sizes in the wide population vary between 125 ml and 1900 ml, an array design that provides the highest number of coils and the highest filling factor for each subject may be difficult to design. The present approach addresses these issues and provides, in one embodiment, a breast coil array having an increased number of channels (e.g., more than 8 channels, such as 31 channels) that is suitable for 3 Tesla (T) imaging. In one such implementation, the breast receive coil array is flexible and conforms to different breast sizes, therefore preserving a high filling factor for all subjects.

Figure 1:
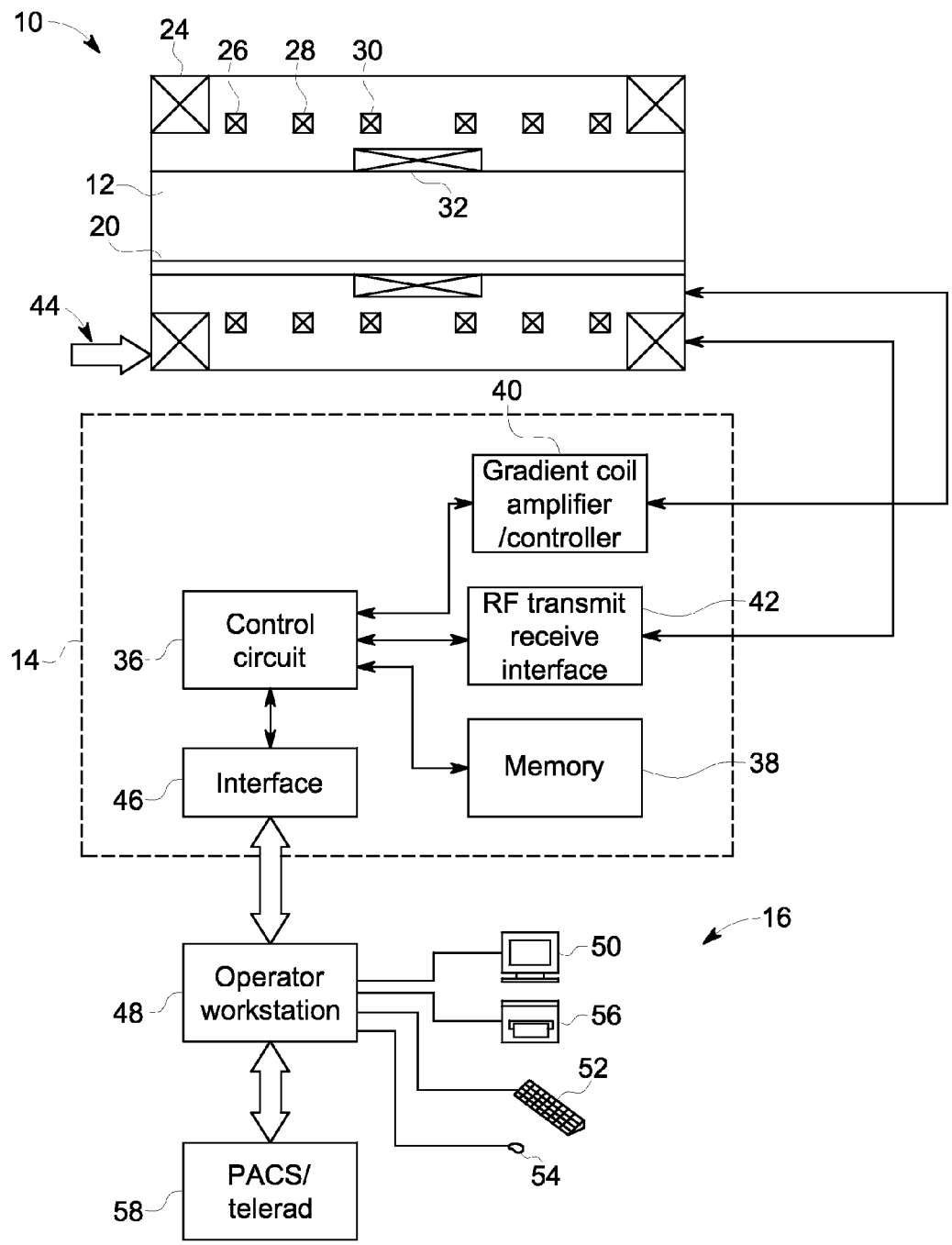
FIG. 1 is an illustration of an embodiment of an MRI system utilizing one or more gradient coils, in accordance with aspects of the present disclosure.

With the foregoing discussion in mind, and turning now to the drawings, FIG. 1 depicts an embodiment of an MRI system 10 suitable for use with the receive coil discussed herein. The MRI system 10 is illustrated diagrammatically as including a scanner 12, scanner control circuitry 14, and system control circuitry 16. While the MRI system 10 may include any suitable MRI scanner or detector, in the illustrated embodiment the system includes a full body scanner having a table 20 positioned to place a patient in a desired position for scanning. In one embodiment, the table 20 can accommodate a patient lying face downward on the table with the breasts hanging pendant in separate receive coil array assembly, as discussed herein.

The scanner 12 may include a series of associated coils for producing controlled magnetic fields, for generating radio frequency (RF) excitation pulses, and for detecting signals from nuclear spins within the patient in response to such pulses. In the diagrammatical view of FIG. 1, a main magnet 24 is provided for generating a primary magnetic field. A series of gradient coils 26, 28 and 30 are grouped in one or more gradient coil assemblies for generating controlled magnetic gradient fields during examination sequences. A transmit RF coil 32 is provided for generating RF pulses for exciting the nuclear spins. Power may be supplied to the scanner 12 in any appropriate manner, as indicated generally at reference numeral 44. The RF coil 32 may be driven by driving circuitry within the system 10. In addition, receiving circuitry may be present in the system 10 for communicating with a separate receive coil array (i.e., a breast receive coil array as discussed herein) for receiving signals from the nuclear spins. As will be appreciated, receiving coils may be provided in any suitable physical configuration, including phased array coils.

In accordance with an embodiment, the gradient coils 26, 28, and 30 may each be formed using conductive wires, bars, plates or sheets to form a coil structure, which generates a gradient field upon application of control pulses. The placement of the gradient coils 26, 28, and 30 within the gradient coil assembly may be done in several different orders and with varying configurations, and the scanner 12 may further include complementary gradient coils to shield the gradient coils 26, 28, and 30. In some embodiments, the gradient coil 26 may be a z-gradient positioned at an outermost location compared to the gradient coils 28 and 30. The gradient coils 28 and 30 may be x-axis and y-axis coils, respectively.

The gradient coils 26, 28, and 30 of the scanner 12 may be controlled by external circuitry to generate desired fields and pulses, and to read signals from the nuclear spins in a controlled manner. The gradient coils 26, 28, and 30 may also serve to generate precisely controlled magnetic fields, the strength of which vary over a predefined field of view, typically with positive and negative polarity. When each gradient coil 26, 28, or 30 is energized with known electric current, the resulting magnetic field gradient is superimposed over the primary field and produces a desirably linear variation in the axial component of the magnetic field strength across the field of view. The field may vary linearly in one direction, but may be homogenous in the other two. The three gradient coils 26, 28, and 30 may have mutually orthogonal axes for the direction of their variation, enabling a linear field gradient to be imposed in an arbitrary direction with an appropriate combination of the three gradient coils 26, 28, and 30.

The pulsed gradient fields may perform various functions integral to the imaging process. Some of these functions are slice selection, frequency encoding and/or phase encoding. These functions can be applied along the x-, y- and z-axes of the original coordinate system or along other axes determined by combinations of pulsed currents applied to the individual field coils.

The coils of the scanner 12 are controlled by the scanner control circuitry 14 to generate the desired magnetic field and radiofrequency pulses. In the embodiment of FIG. 1, the control circuitry 14 thus includes a control circuit 36 for commanding the pulse sequences employed during the examinations, and for processing received signals. The control circuit 36 may include any suitable programmable logic device, such as a CPU or digital signal processor of a general purpose or application-specific computer. Further, the control circuit 36 may include memory circuitry 38, such as volatile and/or non-volatile memory devices for storing physical and logical axis configuration parameters, examination pulse sequence descriptions, acquired image data, programming routines, and so forth, used during the examination sequences implemented by the scanner 12.

Interface between the control circuit 36 and the coils of the scanner 12 may be managed by amplification and control circuitry 40 and by transmission and receive interface circuitry 42. The amplification and control circuitry 40 includes amplifiers for each gradient field coil 26, 28, and 30 to supply drive current in response to control signals from the control circuit 36. The receive interface circuitry 42 includes additional amplification circuitry for driving the RF coil 32. A power supply, denoted generally by reference numeral 44 in FIG. 1, is provided for energizing the primary magnet 24. Finally, the scanner control circuitry 14 includes interface components 46 for exchanging configuration and image data with the system control circuitry 16.

The system control circuitry 16 may include a wide range of devices for facilitating interface between an operator or radiologist and the scanner 12 via the scanner control circuitry 14. In the illustrated embodiment, for example, an operator workstation 48 is provided in the form of a computer workstation employing a general purpose or application-specific computer. The operator workstation 46 also typically includes memory circuitry for storing examination pulse sequence descriptions, examination protocols, user and patient data, image data, both raw and processed, and so forth. The operator workstation 48 may further include various interface and peripheral drivers for receiving and exchanging data with local and remote devices. In the illustrated embodiment, such devices include a monitor 50, a conventional computer keyboard 52, and an alternative input device such as a mouse 54. A printer 56 is provided for generating hard copy output of documents and images reconstructed from the acquired data. In addition, the system 10 may include various local and remote image access and examination control devices, represented generally by reference numeral 58 in FIG. 1. Such devices may include picture archiving and communication systems, teleradiology systems, and the like.

As noted above, the present disclosure relates generally to receive coil arrays suitable for use in breast imaging with an MRI system. In certain embodiments, the receive coil array is suitable for 3T imaging and is provided as separable or decoupled mechanical (i.e., a mechanical support structure) and electrical components (i.e., a receive coil array), allowing different mechanical support structures to be used for different patients without redesign of the flexible receive coil array housing.

Figure 2:
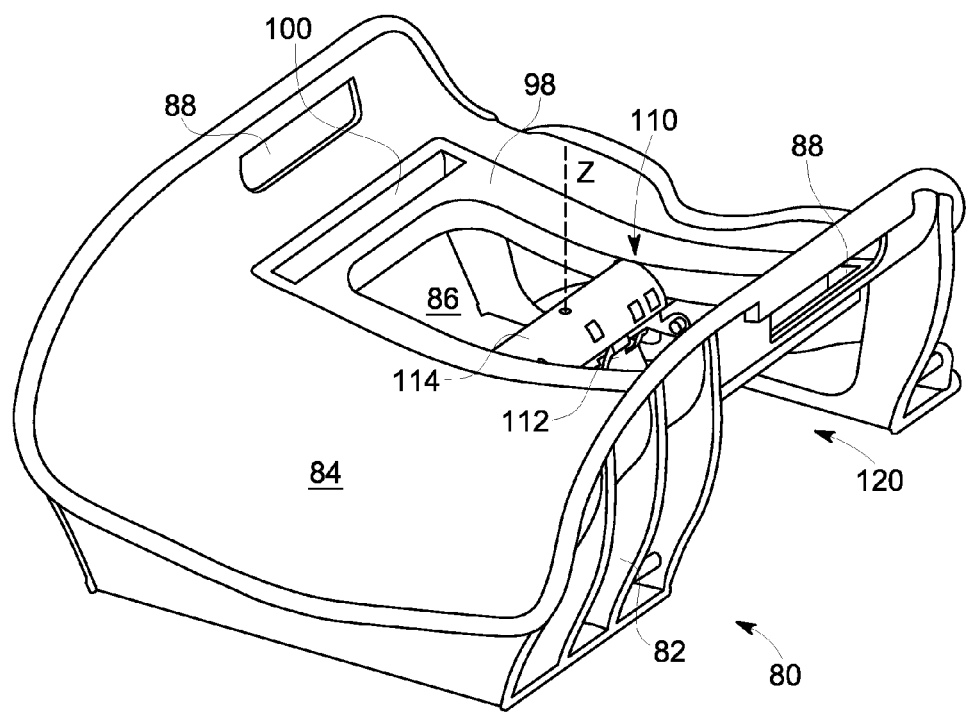
FIG. 2 is a perspective view of an example of a mechanical support structure and constituent components, in accordance with aspects of the present disclosure.

For example, turning to FIG. 2, a mechanical assembly 80 is depicted having multiple, separable components. In the depicted example, a primary housing or support component 82 is provided to which the other components may be connected or coupled. The housing component 82 may be made of plastic or other materials suitable for use in the environment of an MRI imaging system 10. In this example, the housing component 82 includes a patient facing surface 84 on which the patient will lie. An opening 86 is provided in the patient facing surface 84 through which the breasts of the patient may hang pendant when the patient lies on the patient facing surface 84. In the depicted example, the housing component 82 also includes handles or hand holds 88.

The depicted mechanical assembly 80 also includes a removable insert 98 that may be fitted into the opening 86. The insert 98 may be made of plastic or other materials suitable for use in the environment of the MRI imaging system 10. In practice, a variety of differently sized inserts 98 may be provided, with the appropriately sized insert 98 being placed in the opening 86 to accommodate the breasts of the current patient and to provide comfort and support to the patient while also conforming the flexible coil array (i.e., the electrical components) of the coil assembly to the breasts of the patient. In the example shown in FIG. 2, the insert include slots 100 along the sides through which the electrical components may pass when fitted to the patient, as discussed below.

Also depicted is a medial insert (i.e., sternum support) 110. The depicted example of a sternum support 110 includes two parts, a support component 112 and an overlying component 114, that may be separable or movable relative to one to allow the electronic component to be inserted and held in place between the two. In practice, the sternum support 110 acts to hold the electrical components in proximity or contact with the medial surfaces of the breast during imaging. As with the other components of the mechanical assembly 80, the sternum support 110 and its component pieces may be made of plastic or other materials suitable for use in the environment of the MRI imaging system 10. In certain embodiments, the sternum support 110 may be movable with respect to an axis (i.e., a x-axis) of the housing component 82 that passes through the opening 86 such that the sternum support 110 can be moved higher or lower with respect to the opening 86 and/or insert 98 to accommodate patient breast size and to provide comfort and support to the patient while also properly positioning the electrical components with respect to the medial breast surfaces. In one embodiment, the sternum support 110 may be moved higher or lower with respect to the opening 86, such as up to about 1.5 inches.

Figure 3:
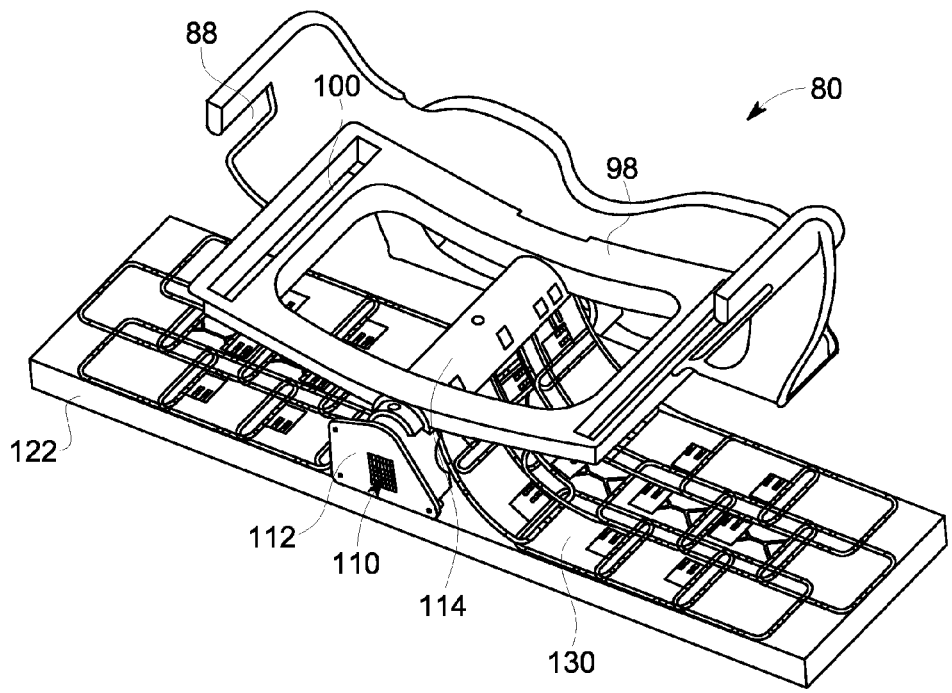
FIG. 3 is s partial cutaway perspective view of the mechanical support of FIG. 2 along with a flexible receive coil array, in accordance with aspects of the present disclosure.

Turning to FIG. 3, a partial cut-away view of the mechanical assembly 80 is depicted. In the depicted example, a foam cover or other flexible cover 122 is depicted as also being present and as covering the exposed surface of the electrical component assembly 130. Such a cover 122 may cover and protect the electrical assembly 130, such as protecting cables and/or components associated with the electrical assembly 130. The electrical assembly 130 and associated flexible cover 122 may be raised and lowered (i.e., is movable) with respect to the housing component 82 to fit within or conform to lateral side openings 120 defined by the housing component 82 and to compress the breast when in place during imaging. In one embodiment, the cover 122 supports and/or protects the electrical components 130, when present and conforms the electrical components 130 (i.e., the receive coil array) to the lateral sides of the breast during imaging. In one embodiment, the sternum support 110 is provided adjacent the flexible cover 122 and helps to conform the electrical components 130 to the medial surfaces of the breast during imaging.

In certain imaging configurations or protocols, the flexible cover 122 and electrical components 130 may be moved, e.g., lowered, (as depicted in FIG. 3) with respect to the housing component 82 on one or both sides to allow lateral access to the breasts during imaging. Similarly, in certain imaging configurations or protocols the flexible cover 122, and the medial insert 110, may be lowered or otherwise moved to allow medial or frontal access to the breast that might otherwise be blocked by the medial insert 110. In such implementations, when the flexible cover 122 is moved to allow lateral or medial access during imaging, receive coils on the electrical components 130 may still be present on the opposing surfaces of the breast, allowing the breast to continue to be imaged while the physician or other caregiver has access to the breast, such as to perform a biopsy.

Figure 4:
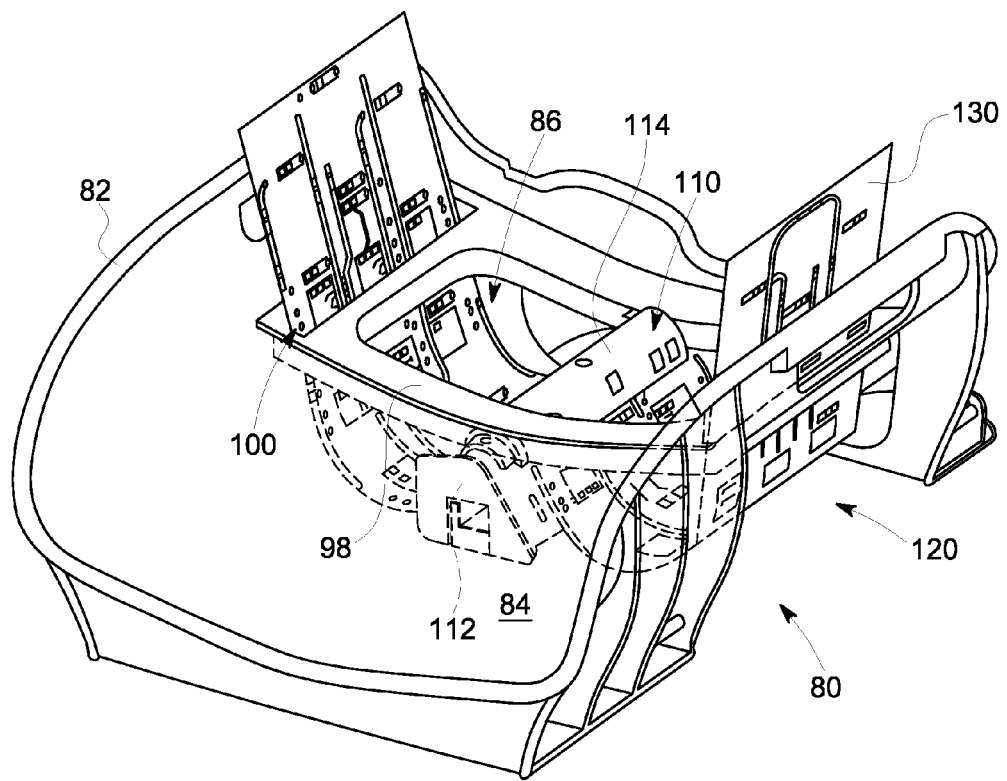
FIG. 4 is a perspective view of the mechanical support of FIG. 2 along with a flexible receive coil array, in accordance with aspects of the present disclosure.

Turning to FIG. 4, a view of the mechanical assembly 80 in conjunction with the electrical components 130 is depicted. To provide visibility of the threading of the electrical components 130 through the mechanical assembly 80, the flexible cover 122 is omitted from the view. As depicted in this example, a medial portion of the electrical components 130 is secured between the support components 112 and the overlying component 114 of the sternum support 110. Placement and adjustment of the sternum support 110 within the opening 86 therefore acts to conform the proximate surfaces of the electrical component 130 to the medial surfaces of the breast for imaging. In addition, the ends of the electrical component 130 are movably threaded through the slots 100 of the insert 98. In this way, the electrical component 130 may be pulled through the slot 100 to achieve the desired degree of conformity and/or proximity between the electrical component 130 (i.e., the receive coils) and the medial and lateral surfaces of the breasts. Thus, in certain implementations, for patients with smaller breasts the ends of the electrical components may extend to or cover the side of the torso or even extend to the back of the patient. In such an example, certain receive coils present on the electrical component 130 that are not adjacent or proximate to the breasts may be turned off during an imaging session.

Figure 5:
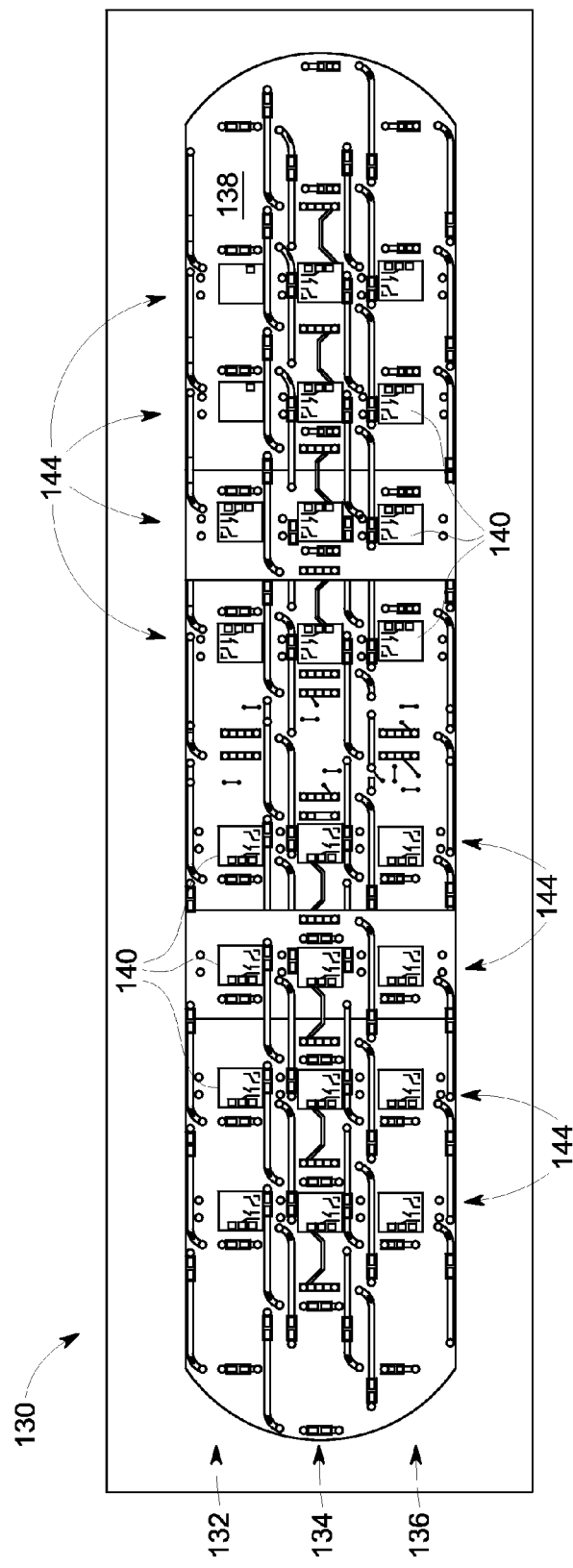
FIG. 5 depicts a plan view of a flexible receive coil array, in accordance with aspects of the present disclosure.

While the preceding discussion relates generally to the mechanical assembly 80 and its constituent components and use, the electrical component 130 is discussed in greater detail in FIG. 5 and in following figures. As noted herein, an example of a suitable receive coil array for use in accordance with the present approach may have 8 or more receive coils and associated channels and may be suitable for use with a 3 Tesla (T) imaging system. By way of example, certain implementations discussed herein may have twice or more than twice the number of coils found in a conventional 8 coil array, such as the depicted 31 channel breast coil of FIG. 5. In one embodiment, the electrical component includes 31 receive coils that are approximately square in shape and approximately 3.5 inches on each side and that are arranged in three rows along the superior/inferior direction, a top row 132 having 10 coils, a middle row 134 having 11 coils, and a bottom row 136 having 10 coils, each coil corresponding to a respective channel. In one embodiment, the overlap between neighboring coils may be staggered going from the sternum to the axilla for better imaging coverage.

In the depicted example, the electrical component 130 on which the receive coils are provided includes a flexible substrate 138, such as in the form of a coated flex circuit or similar flexible circuitry substrate. In certain embodiments, a foam spacer or pad (such as a 1.0 to 1.5 cm thick foam spacer) may be provided on the patient facing surface of the substrate 138 so that substrate itself (and the electrical components integrated with the substrate) do not directly contact the patient when in use.

In one example, eight pads 140 are provided on each row and serve as support structures for the circuitry for the coil array. In a further embodiment, the major electrical components of the coil (e.g., tuning caps, diodes, baluns, inductors, capacitors) of the receive coil array may be disposed in a set of linear arrangements (e.g., along lines 144) running in the superior/inferior direction and protected by a mechanical rib or protector, as discussed below. Such ribs, when present may serve to mechanically protect the linear arrangements of electrical components while still allowing the substrate 138 (and associated electrical components) to bend in the right-left direction, thus allowing the substrate 138 to conform to and wrap around a patient when in use.

Figure 6:
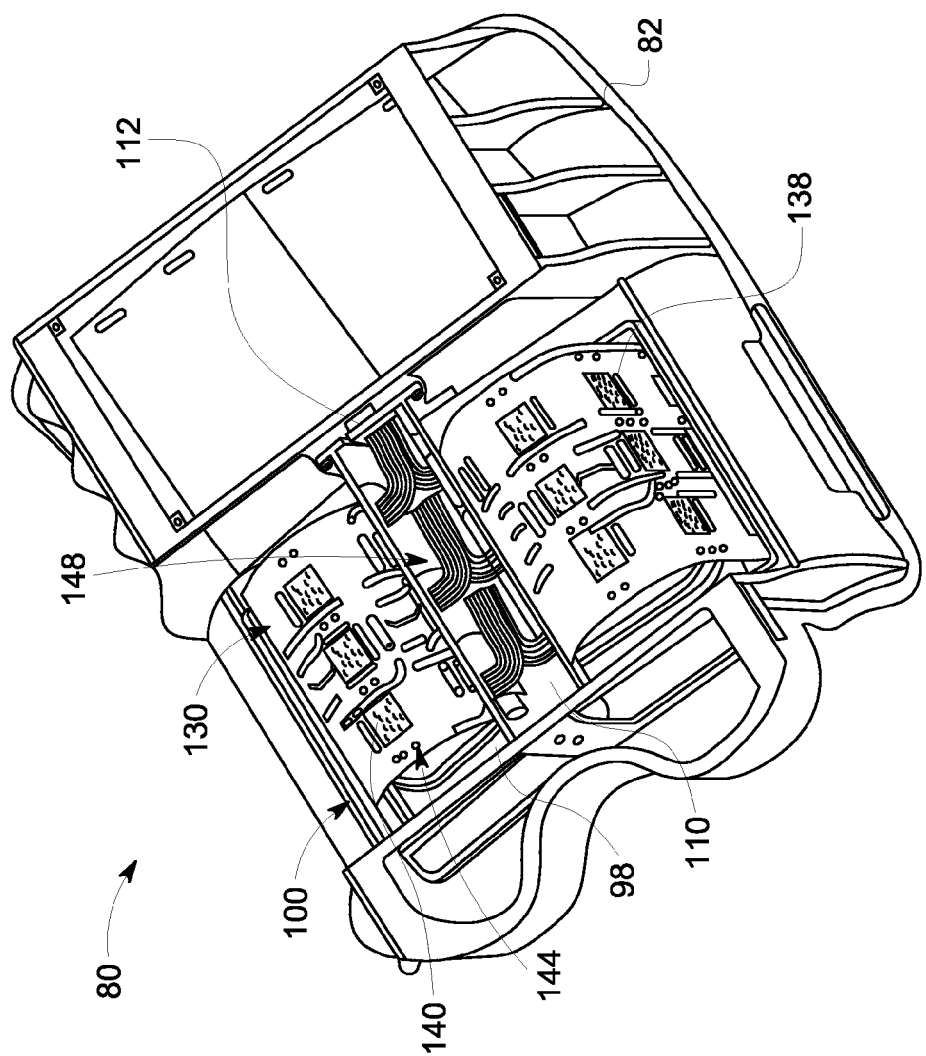
FIG. 6 is a perspective view of the mechanical support of FIG. 2 and the receive coil array of FIG. 5 when combined and as seen from a different perspective, in accordance with aspects of the present disclosure.

Turning to FIG. 6, an association of the electrical components 130 of a receive coil array are again depicted in association with a mechanical assembly 80, including being threaded through slots 100 of insert 98. In this depiction the mechanical assembly 80 and electrical components 130 are seen from below, i.e., opposite the patient facing surface 84. In this example, the connective wiring 148 is depicted that interconnects to conductive structures on the substrate 138 and allows readout of signals generated by the coils within the substrate 138. For example, as depicted, cables and/or conductive structures 148 may be routed through holes or passages provided in the housing component 82 and/or sternum support 110 to interface with conductive structures on the flexible substrate 138 where the substrate 138 is adjacent to the sternum support 110. In one such implementation, the cables 148 entering the sternum area are routed toward the abdominal area of the patient, where preamplifiers or other downstream electrical circuitry may be located.

Figure 7:
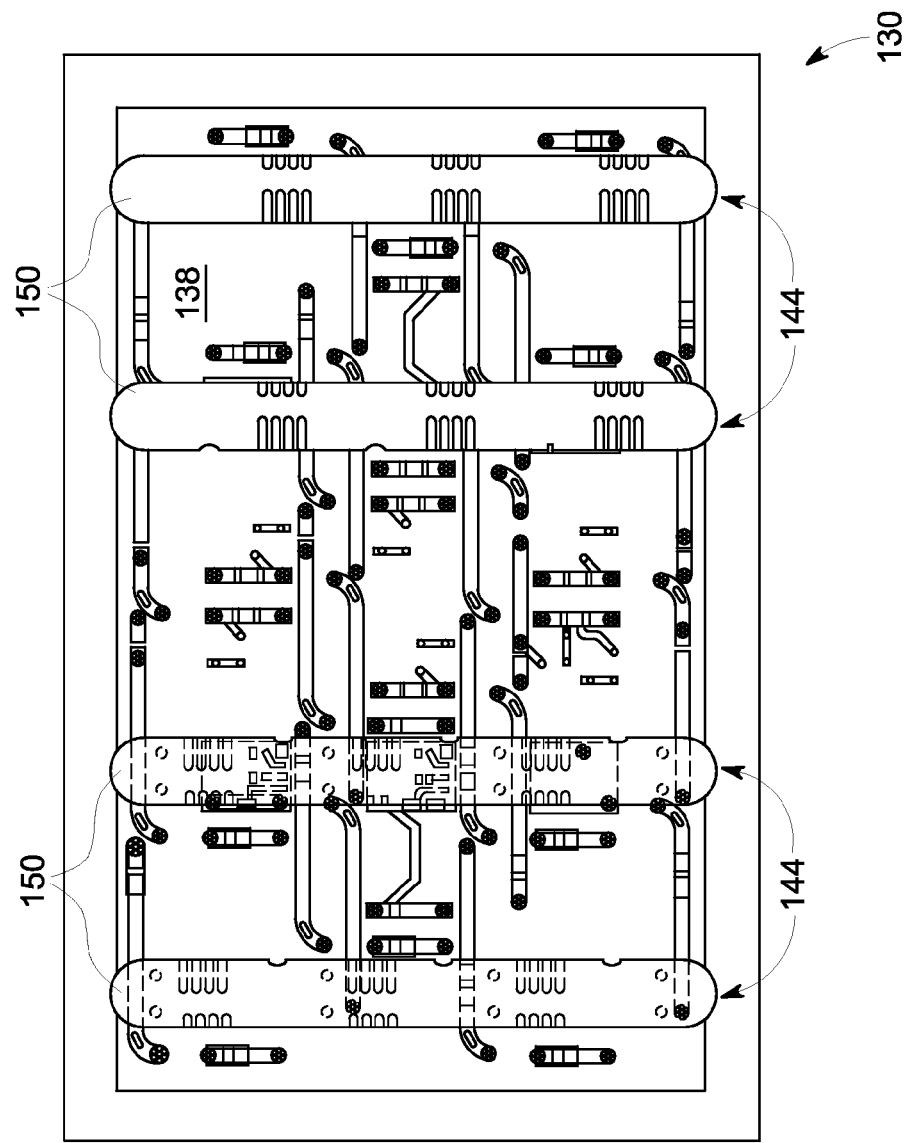
FIG. 7 depicts a portion of a flexible receive coil array fitted with mechanical ribs or protectors, in accordance with aspects of the present disclosure.

Turning to FIG. 7, one arrangement is depicted with respect to a portion of substrate 138 along with corresponding protectors or ribs 150 that may be mechanically attached to the substrate 130 to cover and protect the lines 144 of electrical components, as mentioned above. The ribs 150 may be made of plastic or other materials suitable for use in the environment of an MRI imaging system 10. In the depicted example, the two ribs 150 in the leftmost portion of the figure are depicted as semi-transparent to allow visualization of the underlying lines 144 of electrical components that are protected by the ribs 150. The ribs 150 may be sized and placed such that, when attached to the substrate 138, the combined substrate 138 and ribs 150 may pass through and be movable with respect to slots 100 of the insert 98 to allow adjustment of the receive coil array (e.g., electrical components 130) with respect to the breasts of the patient.

With the foregoing discussion of implementations of structural and electrical components in mind, it may be noted that in certain such implementations, a signal-to-noise ratio can be achieved that is at least twice what is achieved using a conventional 8 channel coil assembly for the same scan. Further, in such experiments, significantly lower geometry factors (i.e., g-factors) can be achieved compared to comparable 8 channel coil arrangements, indicating that examinations can be performed at an accelerated pace relative to examinations performed using a conventional 8 channel coil assembly.

In particular, various studies were performed using implementations of a breast receive coil array as discussed herein. For example, in one set of studies, nine spherical phantoms were utilized to investigate how the tuning and matching of each coil change as a function of breast size and composition using a breast coil assembly as discussed herein. In this study, three sets of 3 identical phantoms, having volumes of 225 ml, 525 ml, and 1700 ml respectively, were filled with water (+1.1 g/L $CuSO_4$) and 0 g/L, 1.1 g/L, or 2.2 g/L NaCl respectively. The sizes and salt concentrations of the phantoms were designed so as to be representative of sizes and breast compositions in a general population of subjects and are shown in the first two columns of Table 1 (see below). The tuning and matching of the coil elements were analyzed as a function of phantom.

TABLE 1

| S11 [dB] for all right center coils of a test breast receive coil array | | | | | | |
|---|---|---|---|---|---|---|
| Phantom | NaCL Conc. | Ch1 | Ch2 | Ch3 | Ch4 | Ch5 |
| Small (225 ml) | 0 | 30.1 | 32.7 | 36.6 | 30.6 | 24.5 |
|  | 1.1 g/L | 30.1 | 32.7 | 36.6 | 30.1 | 24.6 |
|  | 2.2 g/L | 30.1 | 32.7 | 36.6 | 29.3 | 24.6 |
| Medium (525 ml) | 0 | 30.1 | 33.2 | 36.7 | 27.7 | 24.8 |
|  | 1.1 g/L | 30.2 | 33.3 | 36.6 | 27.4 | 24.6 |
|  | 2.2 g/L | 30.1 | 33.3 | 36.7 | 27.4 | 24.5 |
| Large (1700 ml) | 0 | 32.2 | 34.7 | 38.4 | 24.9 | 25.7 |
|  | 1.1 g/L | 32.1 | 33.4 | 37.3 | 24.5 | 25.1 |
|  | 2.2 g/L | 32.1 | 32.5 | 36.3 | 24.8 | 24.6 |

With this study methodology in mind, Table 1 presents the S11 for all five coils of the right center row of the array starting with the outermost (Ch1) and ending with the sternum coil (Ch5) as a function of "breast" size and loading. As evidenced by Table 1, relatively limited change in tuning/matching occurs for drastic changes in anatomy, confirming suitable performance of the breast receive coil described herein in a range of body types. Thus, the study related to Table 1 supports the position that a breast coil receive array, as disclosed herein, remains tuned and matched in any configuration In another study, two additional scenarios were analyzed. In these additional scenarios, the performance of a presently disclosed breast receive coil array was positioned and tested on a torso phantom with the two medium size (~500 ml) spheres (each filled with 1 g/L $CuSO_4$ and 1.1 g/L NaCl) positioned as breasts with respect to the torso phantom. In the first setup, the receive coil array was tightly wrapped around the setup for evaluation, i.e., the substrate 138 was drawn tight against phantom breasts and torso. In the second setup, the receive coil array was only loosely wrapped around the spherical breast phantoms, allowing most of the coils to pick up some signal from the breast spheres, at the expense of reducing the filling factor for each coil. That is, the first setup simulated a higher filling factor arrangement while the second setup simulated a reduced or lower filling factor arrangement. Signal-to-noise ratio maps and g-factor maps were generated for both configurations. Further, in vivo images were also obtained in both configurations (i.e., tight and loose), using a 3D spoiled GRE sequence (TE/TR=1.7/3.8 ms). All experiments were performed on a GE MR750 3T system.

With respect to this study g-factor maps (acceleration factor r=4 in the R/L direction) and SNR maps for the 2 setups were generated. Based on these maps, higher g-factors and lower SNR were associated with the loose configuration (i.e., lower filling factor) in the breast area. This trend was confirmed in vivo, where 15-20% lower SNR was consistently noted in the breast area of the volunteer, scanned using the 3D SPGR sequence. These results indicate that high filling factor configurations (where the receive coil array conforms to the breast surface) are more suitable for obtaining breast images, and supports the use of a flexible breast array, as discussed herein, as a suitable configuration for breast imaging.

Further, in other studies it has been determined that an increase in the number of channels (such as to 31 channels from 8 channels in certain implementations) allows significantly higher capability of accelerating imaging. For example, for a 31 channel coil, as discussed herein, g-factors of less than 1.25 were observed for acceleration factors of up to 6. Such acceleration factors could allow higher temporal resolution dynamic contrast enhanced (DCE) imaging, which in turn allows better kinetic modeling of data and higher specificity in cancer detection.

Technical effects of the invention include a receive coil array for use in breast imaging. In certain embodiments, the receive coil array has more than 8 receive coils and associated channels, such as 31 receive coils and channels. In certain implementations, the receive coil array is provided as a flexible array that is separable from a mechanical support that is configurable to the patient. The adjustability and separability of the receive coil array relative to the mechanical support allows the receive coil array to substantially conform to the breasts of the patient during imaging, thereby providing a high filling factor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A breast imaging assembly for use in a magnetic resonance imaging system, the assembly comprising:
   a mechanical assembly comprising:
      a patient facing surface configured to support a patient in a breast imaging position;
      an opening within the patient facing surface through which the breasts of the patient pass when the patient is supported by the mechanical assembly; and
      a removable insert configured to fit within the opening, the removable insert comprising slots;
   an electrical assembly that is separable from the mechanical assembly, the electrical assembly comprising:
      a flexible substrate configured to removably couple to the mechanical assembly through the slots to conform around medial and lateral surfaces of a patient's breasts; and
      a plurality of receive coils embedded within the flexible substrate.

2. The breast imaging assembly of claim 1, wherein the mechanical assembly comprises a housing component having the patient facing surface and opening, wherein the housing component further comprises a lateral opening on either side of the opening.

3. The breast imaging assembly of claim 1, wherein the mechanical assembly comprises a sternum support configured to fit within the opening so as to divide the opening into two respective portions.

4. The breast imaging assembly of claim 3, wherein the sternum support is adjustable along an axis running through the opening.

5. The breast imaging assembly of claim 1, wherein the electrical assembly comprises a plurality of linear arrangements of electrical components within the flexible substrate.

6. The breast imaging assembly of claim 5, further comprising a plurality of ribs, wherein each rib is configured to affix to the flexible substrate over at least one of the plurality of linear arrangements of electrical components.

7. The breast imaging assembly of claim 1, wherein the electrical assembly further comprises a foam spacer disposed on the flexible substrate.

8. The breast imaging assembly of claim 1, wherein the plurality of receive coils comprises more than 8 receive coils.

9. The breast imaging assembly of claim 1, wherein the plurality of receive coils comprises 31 receive coils.

10. The breast imaging assembly of claim 1, wherein the plurality of receive coils is arranged as three rows of receive coils.

11. A mechanical support for breast imaging, comprising:
   a housing component, comprising:
      a patient facing surface;
      an opening defined in the patient facing surface; and
      a lateral opening on either side of the opening;
   a sternum support configured to fit within the opening such that, when fitted within the opening, the sternum support divides the opening into two respective portions;
   a removable insert configured to fit within the opening, the removable insert comprising slots through which ends of a removable electrical assembly are treaded to conform around medial and lateral sides of a patient's breast.

12. The mechanical support of claim 11, wherein the sternum support comprises a support component and an overlying component that are movable or removable with respect to one another.

13. The mechanical support of claim 11, wherein the sternum support is configured to be adjusted along an axis running through the opening.

* * * * *